(12) United States Patent
Berenstein et al.

(10) Patent No.: US 6,458,119 B1
(45) Date of Patent: *Oct. 1, 2002

(54) ULTRASOFT EMBOLISM DEVICES AND PROCESS FOR USING THEM

(75) Inventors: Alejandro Berenstein, New York, NY (US); Ivan Sepetka, Los Altos, CA (US)

(73) Assignee: Target Therapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/909,004

(22) Filed: Aug. 8, 1997

Related U.S. Application Data

(60) Continuation-in-part of application No. 08/864,317, filed on May 28, 1997, now Pat. No. 5,826,587, and a division of application No. 07/978,320, filed on Nov. 18, 1992, now Pat. No. 5,690,666, which is a division of application No. 08/436,282, filed as application No. PCT/US93/09914 on Oct. 15, 1993, now Pat. No. 5,718,711.

(51) Int. Cl.[7] .............................................. A61B 17/00
(52) U.S. Cl. ........................................... 606/1; 606/151
(58) Field of Search ............................ 606/1, 191–200, 606/151, 108, 127; 623/1.1, 1.15, 123

(56) References Cited

U.S. PATENT DOCUMENTS

| | | |
|---|---|---|
| 1,341,052 A | 5/1920 | Gale |
| 1,667,730 A | 5/1928 | Green |
| 2,078,182 A | 4/1937 | MacFarland |
| 2,549,335 A | 4/1951 | Rahthus |
| 3,649,224 A | 3/1972 | Anderson et al. |
| 4,512,338 A | 4/1985 | Balko et al. |
| 4,638,803 A | 1/1987 | Rand |
| 4,820,298 A | 4/1989 | Laveen et al. |
| 4,850,960 A | 7/1989 | Grayzel |
| 4,954,126 A | 9/1990 | Wallsten |
| 4,957,501 A | 9/1990 | Lahille et al. |
| 4,994,069 A | 2/1991 | Ritchart et al. |
| 5,064,435 A | 11/1991 | Porter |
| 5,104,404 A | 4/1992 | Wolff |
| 5,108,407 A | 4/1992 | Geremia et al. |
| 5,122,136 A * | 6/1992 | Guglielmi et al. ............ 606/32 |
| 5,133,731 A | 7/1992 | Butler et al. |
| 5,147,370 A | 9/1992 | McNamara et al. |
| 5,151,105 A | 9/1992 | Kwan-Gett |
| 5,176,661 A | 1/1993 | Evard et al. |
| 5,186,992 A | 2/1993 | Kite, III |
| 5,203,772 A | 4/1993 | Hammerslag et al. |
| 5,217,484 A | 6/1993 | Marks |
| 5,536,274 A * | 7/1996 | Neuss ........................ 623/1.42 |
| 5,540,680 A | 7/1996 | Guglielmi et al. |

FOREIGN PATENT DOCUMENTS

| | | | |
|---|---|---|---|
| EP | 0418677 | 3/1991 | |
| FR | 592182 | 7/1925 | |
| WO | WO 92/14408 | * 9/1992 | ................ 623/1.42 |

* cited by examiner

*Primary Examiner*—Glenn K. Dawson
(74) *Attorney, Agent, or Firm*—Lyon & Lyon LLP

(57) ABSTRACT

An exceptionally flexible, ultra-soft vasoocclusive or embolism forming device made of a material which may be a braid, coil, or chain which forms a long, thin thread-like device having little rigidity or column strength. The device is sufficiently flexible and small that it may be hydraulically delivered to a site within the vasculature of a human body using an injected drug or fluid flush through a catheter.

18 Claims, 7 Drawing Sheets

ULTRASOFT EMBOLISM DEVICES AND PROCESS FOR USING THEM

This application is a division of application Ser. No. 08/436,282, filed May 15, 1995 and issued as U.S. Pat. No. 5,718,711 on Feb. 17, 1998, which in turn is a § 371 of PCT/US93/09914 filed Oct. 15, 1993 which in turn claims priority to application Ser. No. 07/978,320, filed Nov. 18, 1992 and issued as U.S. Pat. No. 5,690,666 on Nov. 25, 1997. This application is also a continuation-in-part of application Ser. No. 08/864,317, filed May 28, 1997 now U.S. Pat. No. 5,826,587, which is a divisonal of application Ser. No. 07/978,320, filed Nov. 18, 1992 and issued as U.S. Pat, No. 5,690,666 on Nov. 25, 1997. The disclosures of these applications are hereby incorporated by reference

FIELD OF THE INVENTION

This invention is an exceptionally flexible, ultrasoft vaso-occlusive or embolism forming device. It is made of a radiopaque material which may be a braid, coil, or chain which forms a long, thin threadlike device having little rigidity or column strength. The diameter of the device may be less than about 0.010 inches. The filamentary material making up the device used to form the coil, braid, or chain is typically of a diameter less than about 0.002 inches. The device is sufficiently flexible and small that it may be hydraulically delivered to a site within the vasculature of the human body using an injected drug or fluid flush through a catheter. In some configurations, the device may be delivered using pushers to mechanically deliver the device through the catheter lumen. Various mechanical connections may be used to sever the coil but a simple connection of a dissimilar metal to allow electrolytic separation upon application of a small voltage is desirable. The device assumes a random mass of threadlike material after being ejected from the catheter tip at the chosen vascular site. When the device is a coil, the coil may be a single or of multiple-helices. The device (whether coil or braid or chain) may be used alone or in conjunction with larger coils or braids to achieve a denser occlusion or with fibrous thrombotic attachments or as a substrate to localize the subsequent infusion of tissue adhesives, particulate embolization devices, or chemotherapeutic agents in abnormal blood vessels and tissues. The device may be used for the temporary occlusion of blood vessels during types of diminished blood flow testing. The invention also includes processes for introducing the devices into the human body.

BACKGROUND OF THE INVENTION

Endovascular therapy has been used in treating a variety of different conditions, including control of internal bleeding, occlusion of blood supply to tumors, and relief of vessel wall pressure in the region of aneurysm. A variety of different embolic agents are known as arguably suitable for such therapy.

One known embolic agent includes injectable fluids or suspensions, such as microfibrillar collagen, various polymeric beads, and polyvinyl alcohol foam. The polymeric agents may be additionally crosslinked, sometimes in vivo, to extend the persistence of the agent at the desired vascular site. These agents are often introduced into the vasculature through a catheter. After such introduction, materials there form a solid space-filling mass. Although they provide good short-term vaso-occlusion, they are ultimately reabsorbed in the process of vessel recanalization.

Polymer resins, typically cyanoacrylates, are also employed as injectable vaso-occlusive materials. The resins are typically mixed with a radio-opaque contrast material or made radiopaque by the addition of tantalum powder. Their use is fraught with problems in that placement of the mixture is quite difficult. Inadvertent embolisms in normal vasculature (due to the inability of controlling the destination of the pre-gelled resins) is not altogether uncommon. The material is also difficult or impossible to retrieve once it has been placed in the vasculature. Such resins have not been FDA approved, and a waiver must be requested in each instance where the materials are applied during human operative procedures.

A number of mechanical vaso-occlusive devices are widely used. One such device is a balloon which may be carried to the vessel site at the end of the catheter and there inflated with a suitable fluid, typically a polymerizable resin, and released from the end of the catheter. The balloon device has the advantage that it effectively fills the cross-section of the occluded vessel. However, when using intravascular balloon embolization of intracranial berry aneurysms, inflation of a balloon into the aneurysm carries some risk of aneurysm rupture due to possible "overfilling" of portions of the sac and due to the traction produced when detaching the balloon from the end of the catheter. Moreover, a vascular balloon is difficult to retrieve after the resin within the balloon sets up, and the balloon cannot be easily visualized using radiographic techniques unless it is filled with contrast material. Balloons have also been known to rupture during filling, or release prematurely during filling, or leak monomeric resin into the vasculature during the period before the monomer sets up into polymeric form.

Another type of mechanical vaso-occlusive device is a wire coil or braid which can be introduced through a catheter in stretched linear form and assumes an irregular shape upon discharge of the device from the end of the catheter. A variety of vaso-occlusive coils and braids are known. For instance, U.S. Pat. No. 4,994,069, to Ritchart et al., shows a flexible, preferably coiled, wire for use in small vessel vaso-occlusion. Unlike vaso-occlusive coils previously, Ritchart et al. teaches a coil which is fairly soft and is delivered to the site using a pusher within a catheter lumen. The Ritchart et al. coils are typically pushed into the desired vascular site in a linear configuration. Upon discharge from the catheter, the coil may undertake any of a number of random or regular configurations designed to fill the site. The coils are used for small vessel sites, e.g., 0.5–6 mm in diameter. The coils themselves are said to be between 0.010 and 0.030 inches in diameter. The length of the coiled wire is typically 15–20 times the diameter of the vessel to be occluded. The wire used to make up the coils may be 0.002 to 0.006 inches in diameter. Tungsten, platinum, and gold threads or wires are said to be preferred. These coils have a variety of benefits, including the fact that they are relatively permanent, they can be easily imaged radiographically, they may be located at a well-defined vessel site, and they can be retrieved.

A variation of the mechanical endovascular coil is the electrolytically detached endovascular coil described in U.S. Pat. No. 5,122,132, to Guglielmi et al. Guglielmi's coils are typically used in intracranial aneurysms because of their effectiveness in quickly forming controlled emboli. The disclosed coils are similar to those of Ritchart et al. in size and in composition. However, the method of introducing the coil to the vascular site is somewhat different. Rather than mechanically thrusting the coil into the chosen site, the coil is placed at the site and a small voltage is applied to the guidewire supporting the coil so that the coil is electrolytically detached from the distal tip of the guidewire. The step of electrolytically detaching the coil has the added benefit of forming a thrombus as the coil is detached. Again, as noted above, the Guglielmi coils may be stainless steel or platinum or the like, and are typically 0.010 to 0.020 inches in diameter and are made using wire having approximate diameters of 0.001 to 0.005 inches. The coils in this service are typically between 1 and 50 centimeters in length.

None of this background shows embolism-forming coils, braids, or chains having diameters less than about 0.010 inches in diameter, nor their placement by fluid delivery through a catheter.

SUMMARY OF THE INVENTION

This invention is an exceptionally flexible, ultrasoft vaso-occlusive or embolism device. It may be a braid, coil, or chain and is made of a radiopaque material forming a long, thin threadlike device having little rigidity or column strength. The diameter of the device may be less than about 0.010 inches, preferably less than about 0.0075 inches in diameter. The wire making up the device is typically of a diameter less than about 0.002 inches. The device is sufficiently flexible and small that it may be hydraulically delivered to a site within the vasculature of the human body using a catheter. The device may be mechanically delivered using a pusher wire. The devices may be severed from the pusher wire using a mechanical or electrolytic connection. Because of their flexibility and size, there is little opportunity for friction to develop with the catheter lumen.

These devices may be used with guide wire—directed catheters and with flow directed catheters, even those which are very flexible in their distal regions. This invention provides opportunities for placement of embolism-forming devices in vascular regions otherwise not routinely accessible due to their remote nature.

The device typically assumes a loose, random mass after being ejected from the catheter tip at the selected vascular site. When introduced into a high flow region, the mass quickly compacts into a significantly denser mass. The device, whether coil, braid, or chain, may be used in conjunction with larger coils, braids,or chains to achieve a denser occlusion or as a substrate to localize the subsequent infusion of tissue adhesives, particulate embolization devices, or chemotherapeutic agents in abnormal blood vessels and tissues, or for the temporary occlusion of blood vessels during types of diminished blood flow testing. The device may be coated with thrombotic or therapeutic materials or used in conjunction with fibrous embolic additions to the device. The invention also include processes for introducing the devices into the human body.

This invention is also a method for first introducing a larger vaso-occlusive device, such as a coil, to the vascular site desired by the attending physician, followed by the introduction of the inventive device so as to fill the interstices left by the larger coils and thereby form a denser occlusion. The devices may also be introduced by themselves, if so desired.

DESCRIPTION OF THE INVENTION

Figure 1A:
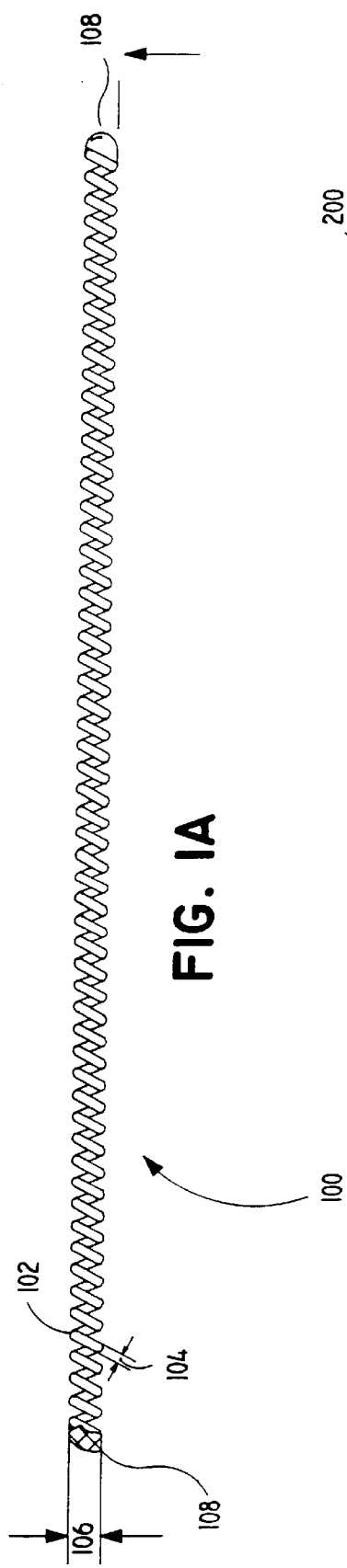
Figure 1A shows an enlarged side view of a coil made according to this invention.

FIG. 1A shows a coil (100) made according to this invention. It is a fairly straightforward device typically formed by wrapping or winding a fine filament or wire (102), preferably having a diameter (104) less than about 0.0025 inches, preferably 0.00045 to about 0.00225 inches, more preferably about 0.0005 to 0.002 inches, most preferably about 0.001 to 0.002 inches, about a spinning mandrel using well-known coil-manufacturing techniques. A separate end cap (108) or termination piece may be included at the end of the coil. The terminator (108) may be a separate piece or a fused portion of the coil or a bit of a filled material such as an epoxy. The major function of the end piece is to prevent the coil from catching on the interior of the catheter lumen or vessel. However, it is acceptable for devices of this size to simply cut the coil ends and not use a terminator (108).

In producing the coil, the coil-manufacturing method is adjusted to produce a single-layer coil typically with a minimum helical pitch, that is to say, the windings are fairly closely packed. Typically, the mandrel will be of such a diameter that the outside coil diameter (106) will be less than 0.010 inches, preferably 0.0014 to 0.0095 inches, more preferably between 0.004 and 0.0095 inches, and most preferably between 0.004 and 0.0075 inches. The soft, flexible coil thus produced is cut to desired lengths after removal from the mandrel. We have found that the device is especially suitable for the noted service when the device (coil, braid, or combination) deflects more than about 20° (preferably more than about 35°) under its own weight over the first centimeter of length, when supported at a single end. The length of the coil may be between 2 mm and 120 cm, typically between 30 cm and 120 cm.

Figure 1B:
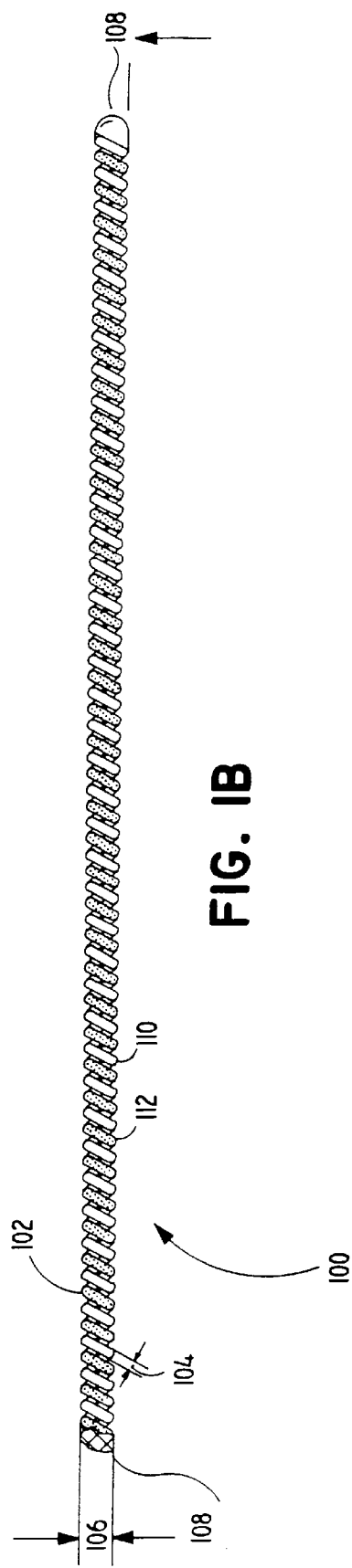
FIG. 1B shows an enlarged side view of a double helix coil made according to the invention.

Instead of the filament shown in FIGS. 1A and 1B, the coil may be produced from a ribbon whose major axis is between 0.001 and 0.002 inches and whose minor axis is 0.0004 and 0.001 inches. Coils produced from ribbons are often moderately stiffer than those produced from similarly sized filaments. Smaller diameter coils are often more readily produced.

The regularity of winding shown in FIG. 1A is not mandatory; the windings may be irregular or of varying pitch. The coil (100) shown in FIG. 1A and 1B (and the variations of the invention which are described below) may be produced from any of a number of different materials. Some portion of the material must be radiopaque so that the coil and its position may be readily monitored within the human vasculature. Suitable materials include biocompatible metals, polymers, and alloys. For instance, biocompatible, radiopaque metals include silver, gold, palladium, platinum, tungsten, iridium, and various stainless steels. Other alloys such as platinum and tungsten (preferably 92% platinum and 8% tungsten) are suitable and, indeed, are often most preferred. The platinum-tungsten alloys desirably have a tensile strength of at least about 180 kpsi and, for a wire of a nominal 0.001" diameter, have a breaking load of 0.17 lb with a minimum elongation of 2% measured at a speed of 1.0 in/min. Various biocompatible polymers including polyethylene, polyurethane, polypropylene, and the like are suitable for use in these devices, but, because of their lack of radiopacity, must usually be teamed with a radiopaque marker or filled with a radiopaque filler to allow proper positioning of the coil within the body. Similarly, other inorganic materials such as fibrous carbon are suitable and may be used in the invention.

After formation of the coil, its interior may be filled with a drug material such as a drug concentrate and its ends partially sealed for slow drug release from the coil in an in vivo aqueous environment. The ends of the coil may be sealed by a water-soluble plug for storage, if so desired. The coil may also (or alternatively) be coated with a thrombotic or medicinal material.

FIG. 1B shows a double helix coil made according to the invention. In this variation, a first coil (110) is wound along with a second coil (112). One of the coils is a fine wire, the second coil may also be a wire or it may be a partially hardened fibrous material, e.g., a material or synthetic fiber, such as Dacron or silk or other thrombotic material. The double helix metallic wire coils made according to this variation of the invention are made using the procedure discussed elsewhere in this document. The double helix coils in which the second coil is a material or synthetic fiber, typically requires some modest heat treatment after winding to set the fiber in the form of its metallic spring colleague. For Dacron or silk, this may be done by steaming the wound spring at reasonably low temperatures, e.g., 300° F. or so, to form the fiber without fusing it.

Figure 2:
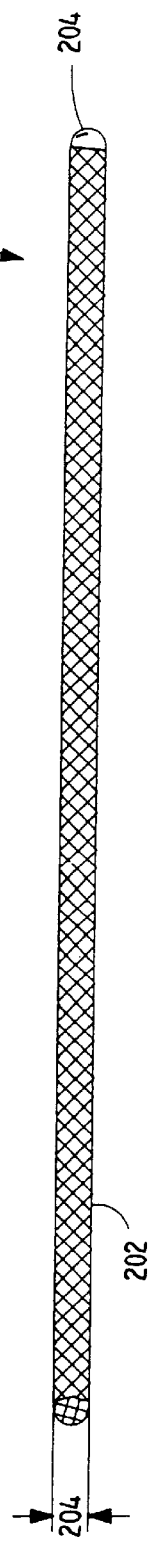
FIG. 2 shows an enlarged side view of a braid made according to this invention.

FIG. 2 shows a braided (or otherwise) woven vaso-occlusive device (200) made according to the invention. The braided occlusive device (200) is tubular and produced by weaving fibers or wires over a mandrel much in the same way the coil of FIG. 1 was made. Woven braids of this size are not common but are made according to known techniques. The wire or fibers in this variation of the invention may be any of the radiopaque or polymeric materials noted above, and additionally the braid may be made of a combination of those materials either alone or in combination with other suitable polymeric or filamentary materials such as Dacron, cotton, or other materials. Organic fibers such as silk, Dacron, or cotton provide a ready substrate for clot formation in the interior region of a vessel. Often the radiopaque portion of the coil provides only a way to anchor the coil onto the vessel wall at the site of release.

The FIG. 2 braid or woven device (200) is of a diameter (204) similar to the coil (106) in FIG. 1. The braid may have a termination piece or section (204) similar in constitution to the analogous portion shown in FIG. 1 above. The length of the braid may similarly be 2 mm to 120 cm.

Figure 3:
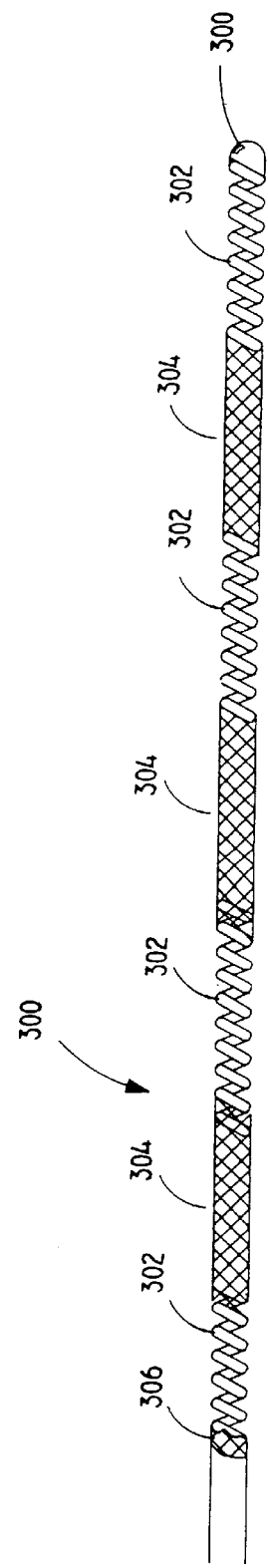
FIG. 3 shows an enlarged side view of a combination coil and braid made according to this invention.

FIG. 3 shows a side view of a combination coil/braid vaso-occlusive device according to the invention. This combination is a sequence of coils (302) and braids (304) similar in make-up and size as the devices shown in FIGS. 1 and 2. Lengths of various coils (302).and braids (304), each often 2 mm to 20 cm in length, are joined together at their respective ends to form the combination device. The overall length of the device, as with those above, may be 2 mm to 120 cm. The device may also have caps or termination pieces (306) on the ends of the device.

Figure 4:
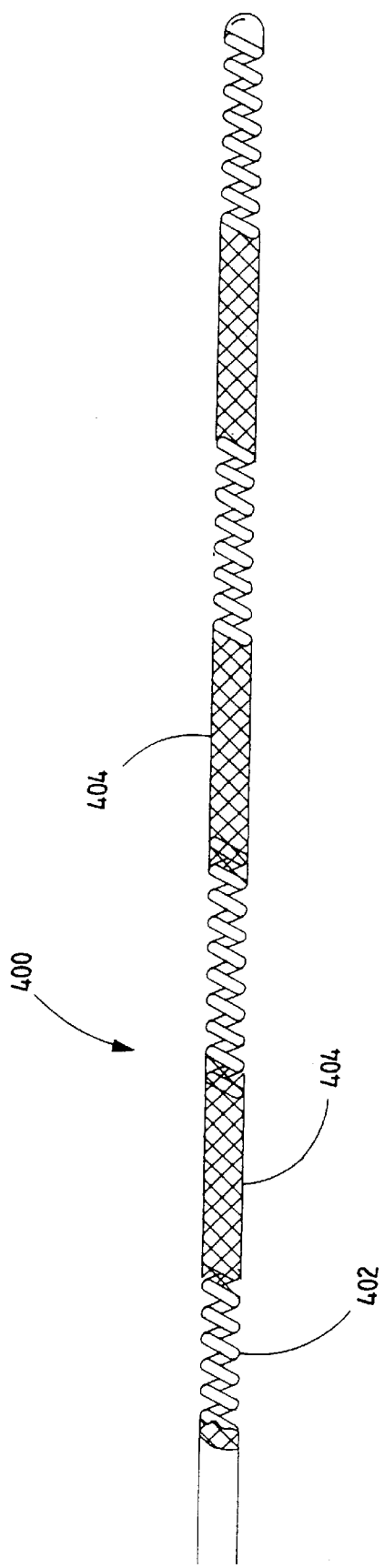
FIG. 4 is a close-up drawing of a variation of the FIG. 3 device in which a braided material is woven on the outside of the coil.

FIG. 4 shows another variation of a coil/braid combination (400). In this variation, however, as is shown by the cutaway insert, the substrate coil is identical to the coil shown in FIG. 1 herein. The braid is woven on the exterior of the coil. In this instance, the braid is more desirably a fibrous material such as Dacron, or cotton. The braid may, however, be a radiopaque material such as the metals and alloys and polymers discussed above. The braid may be joined by welding, melting, or by adhesion to the underlying coil (402).

Figure 5A:
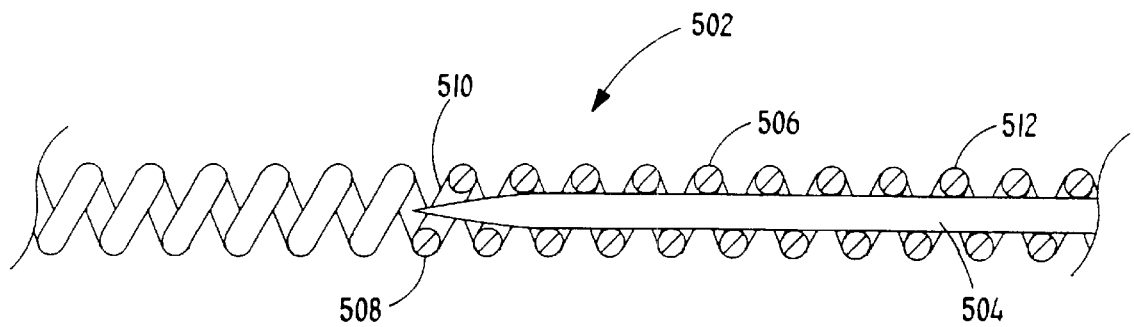
FIGS. 5A and 5B are close-up views of ends of coils made to use electrolytic separation from a wire pusher.
Figure 5B:
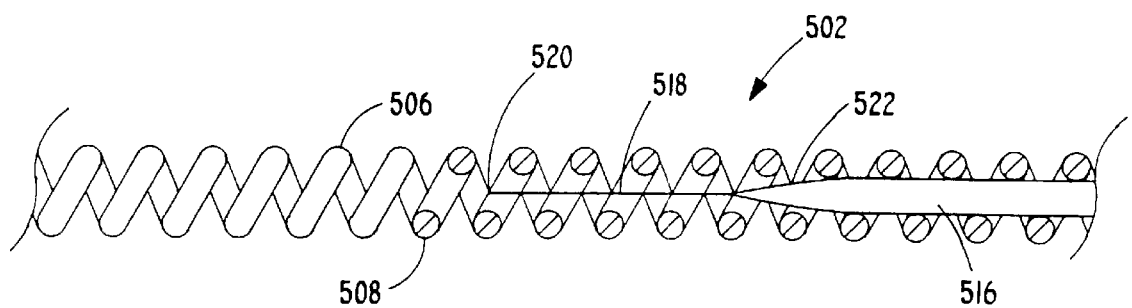

FIGS. 5A and 5B show in partial cutaway, side views of coils which may be delivered using a pusher such as a guide wire and may be detached electrolytically using a procedure, such as that found in Guglielmi et al. as discussed above.

FIG. 5A is a very enlarged side view of one embodiment of this invention in which the guide wire (504) and a portion of the coil of (506) are shown in a partial cross sectional view. A guide wire (504) which may be coated with TEFLON or other suitable insulating material, which coating is not shown, may be placed within a catheter lumen such as is shown in Guglielmi et al. or as is discussed elsewhere in this document. The guide wire (504) typically has a diameter of 0.010 to 0.020 inches diameter in the portion more proximal of the portion shown in the drawing. In the FIG. 5A portion, guide wire (504) is tapered at its distal end to a point (508) within coil (506). Guide wire (504) may be joined at one or more locations, e.g., joint (510) at the distal end or joint (512) proximal of the distal end. These joints (510) and (512) may be made by soldering or the like.

FIG. 5B shows a similar coil guide wire assembly (502) in which a similar guide wire (516) is introduced actually axially within coil (506). The guide wire (516), in this variation, tapers quickly to a very fine wire portion of (518). The most distal portion of a fine wire (518) is joined with coil (506) at junction of (520). Preferably a second joint (522) is made at the proximal end of fine wire (518). This variation of the invention permits substantially greater flexibility than the variation shown in FIG. 5A, at least for the region distal of joint (522). However, the safety factor inherent in having two joints fixing the guide wire or core wire (516) remain in existence.

Because of the significant lack of column strength the coils used and portrayed in FIGS. 5A and 5B, it may be desirable in some instances to introduce the coil not only using respectively guide wires (504) in FIG. 5A and guide wire (516) in FIG. 5B as pushers, but also to move these coils along through the lumen of the catheter using an ancillary saline hydraulic push. The coils of (506) are detached from the respective guide wires (504) and (516) by imposition of a direct current to the guide wires from a power supply exterior to the, body. The current flow from the coils of (506) within the vasculature site causes a thrombus to form by electrothrombosis. Typically, a DC electric current of approximately 0.01 to 2 milliamps at 0.1 to 12 volts as applied to the guide wire. The thrombus forms often within three to five minutes after the imposition of such a voltage. The voltage flows down the guide wire through the insertion means, e.g., the respective conductive joints (e.g.,(510) and (512) in FIG. 5A and (520) and (522) in FIG. 5B) and through the blood or thrombus. The circuit is completed by a negative pole placed in contact with the skin. The coil is detached from the guide wire by electrolytic decomposition of either the joints or some section of the guide wire. For a coil as small as or involved in these inventive devices, the dissolution by electrolytic action normally will take place in less than four minutes. The time of disintegration may obviously be varied by altering the size of the various portions of the guide wire and the area of the guide wire exposed beyond the insulation. The current level may be altered or the flow of conductive fluids such as saline solution may be introduced to enhance the electrolysis rate.

Figure 6A:
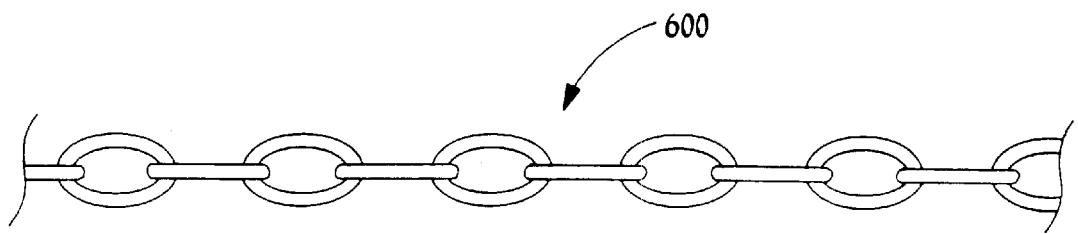
FIG. 6A shows an enlarged side view of a chain made according to this invention and FIGS. 6B and 6C show an inventive chain having attached fibrous material.

FIG. 6A shows a side view of a chain made according to the invention. Chain (600) is produced using typical chain-making techniques. Chains of this size are not common but are easily made according to known techniques. The wire or fibers in this variation of the invention may be any of the radiopaque or polymeric materials noted above. Additionally the chain may be made of a combination of those materials either alone or in combination with other suitable polymeric or filamentary materials such as Dacron, cotton, or other materials. Organic fibers such as silk, Dacron, or cotton provide a ready substrate for clot formation in the interior region of a vessel. The FIG. 6A chain device (600) is of a diameter similar to the coil (106) in FIG. 1. The length of the chain may similarly be 2 mm to 120 cm.

Figure 6B:
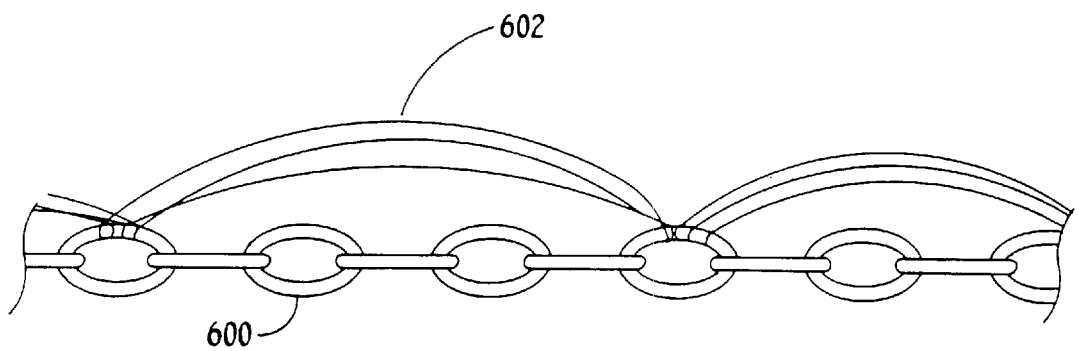

FIG. 6B shows a side view of a chain (600) as shown in FIG. 6A but having suitable polymeric filaments (602) such as Dacron, cotton, or other materials tied to the chain. Organic fibers such as silk, Dacron, or cotton provide a ready substrate for clot formation in the interior region of a vessel. The FIG. 6B fibers (602) are looped from spot to spot on the chain.

Figure 6C:
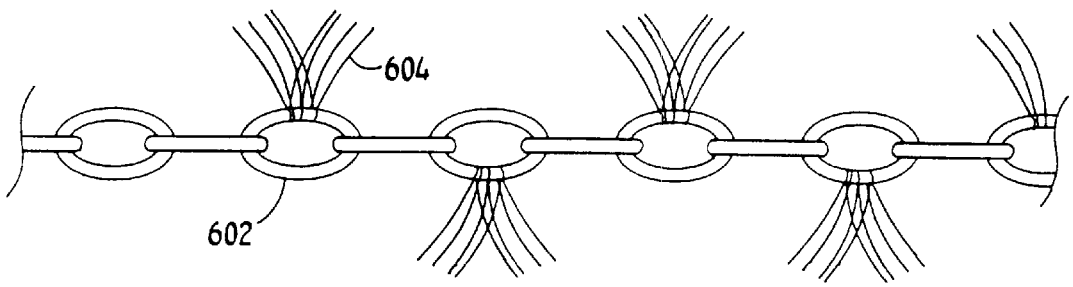

FIG. 6C shows a side view of a chain (600) as shown in FIG. 6A but having polymeric filaments (604) such as discussed above tied to the chain in a brush-like fashion.

Each of the variations discussed above, when provided in the proper size range and materials, is an extremely soft and flexible device, whether the device be coil or braid or chain. These devices exert little if any radial force on the blood vessels into which they are placed. They are sufficiently flexible and small that they may be carried by blood flow after ejection from the distal tip of the catheter by which they are introduced to a narrowing region in the vascular lumen where the device wedges or rolls upon itself and wedges within the blood vessel. The fluid-like properties of the device enables it to conform to the complex geometry of certain fragile, abnormal blood vessels, and in so doing, minimize the risk of causing trauma to or even perforation of those blood vessels. Such flow properties also enable placement of the inventive device at sites in the vasculature currently unreachable by catheterization, such as those within an arteriovenous malformation (AVM).

Although the device is very flexible in all of its configurations, it may be produced having a modest amount of "preform." By "preform" is meant the practice found in Ritchart et al. discussed above, where the coil is bent or crimped in such a way that it assumes a nonlinear shape only after it exits the catheter lumen but passes through the lumen with ease. Such a treatment provides some additional randomness when the coil is placed at its intended site within the vasculature.

Figure 7:
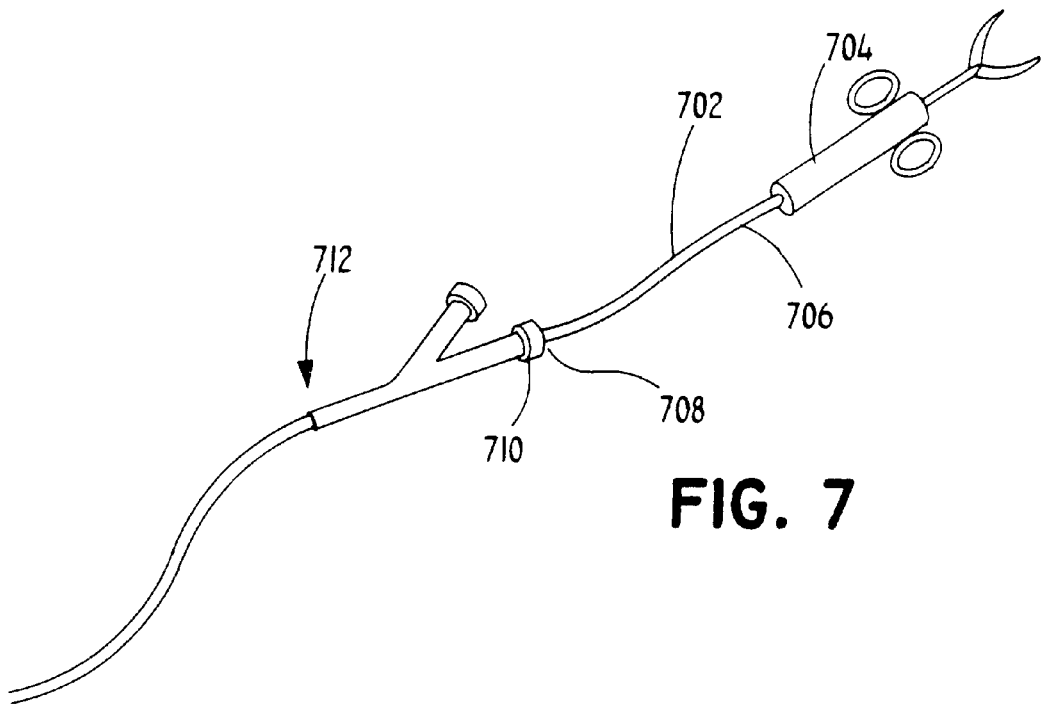
FIG. 7 is a clinical set-up which may be used hydraulically to introduce the coils into the vasculature.

FIG. 7 shows a setup for hydraulically delivering the devices of this invention to a vascular site. In this instance, the devices—coils are depicted—are held in an introducer sheath (702) and delivered through a catheter (712) to the desired site motivated by a syringe (704), containing a suitable fluid. The proximal end (706) of the introducer sheath (702) is connected to the fluid-containing syringe. The distal end (708) of the introducer sheath (702) is introduced to the catheter sidearm accessory (710). The lumen in catheter assembly (712) has been previously cleared of guidewires and other interior constrictions. The plunger on syringe (704) is simply pushed down, and the device within introducer sheath (702) is carried down through catheter (712) to the injection site. After the device is injected to the desired site, additional devices may be injected by swapping another introducer sheath (702) with its related device.

This procedure may be carried out after the catheter has been used to introduce coils of larger size to a particular site. The later introduction of the devices of this invention will enhance the thrombotic potential of the earlier-introduced coil in that the inventive devices will tend to fill the interstices left by the larger coils and achieve a more densely packed occlusion site.

Figure 8:
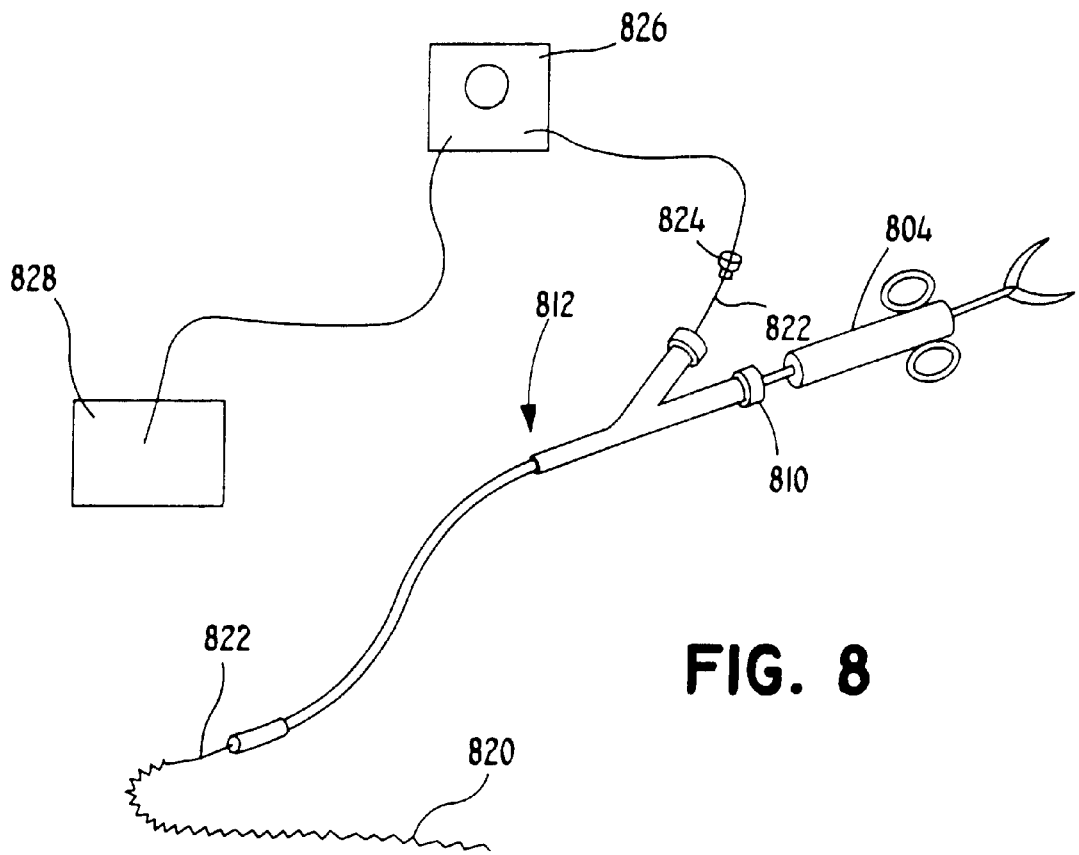
FIG. 8 shows a method for mechanically introducing one or more of the inventive devices into the vasculature.
Figure 9:
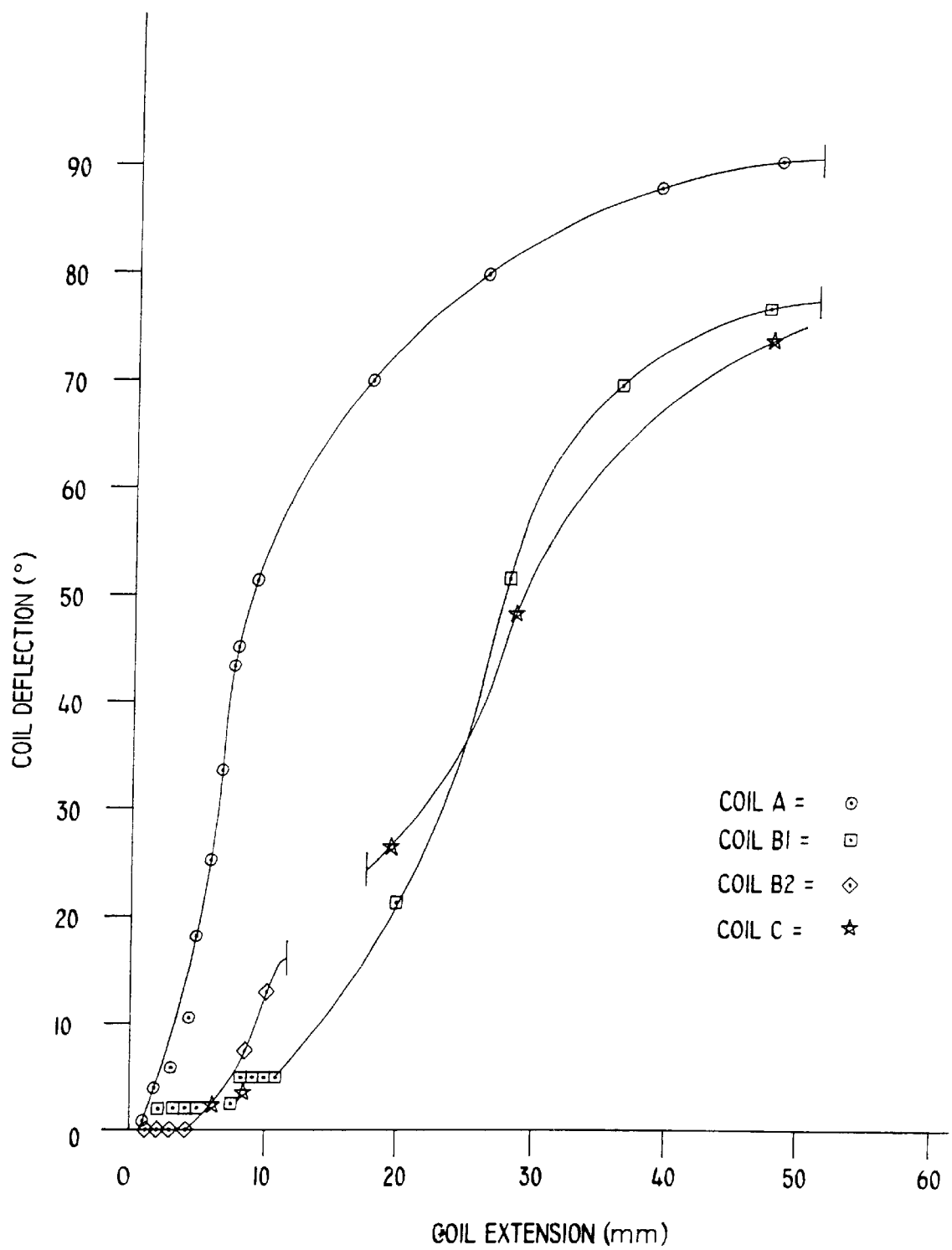
FIG. 9 is a graph comparing deflection versus extension for three coils; one coil made according to this invention and two commercially available embolism coils made generally according to the prior art.

FIG. 8 shows a set-up for delivering coils (820) to a vascular site using a guide wire (822) as a pusher. This arrangement uses a catheter (812) optionally in conjunction with a syringe (804) containing a suitable motivating fluid such as saline solution. At the proximal end in this variation, the optional syringe is attached directly to the catheter hub (810). The guide wire (822) in this variation is shown both extending distally out of the catheter (812) and proximally out of the catheter fitting. A torque device (824) for steering the guide wire or core wire (822) may also be seen. Core wire (822) is in turn attached to power supply (826) at its positive terminal. The negative terminal of power supply (826) is in turn attached to a pad (828) which is applied to the skin to provide a complete circuit to the power supply. The current flows through guide wire (822) to the junction between guide wire (822) and coil (820) (explained in more detail with regards to FIGS. 5A and 5B above) through the thrombus or blood, through the skin back to the pad (828), and then to the power supply. This is used both to create thrombi and to electrolytically sever coil (820) from core wire (822).

Additionally, these processes may include the step of introducing polymer resins, such as cyanoacrylate resins (particularly n-butylcyanoacrylate) to the intended site after the inventive coils, braids, and chains are in place. Said another way, the. inventive devices form a substrate for these tissue adhesives, or particulate embolization materials such as microparticles of polyvinyl alcohol foam, or various chemotherapeutic agents. The catheters suitable for use in introducing these devices are discussed in significant detail in U.S. Pat. No. 4,994,069, to Ritchart et al., as was discussed above.

EXAMPLE

This example demonstrates the significant difference between a preferred embodiment of this inventive coil and similar commercial coils of the type discussed in Ritchart et al. The example shows how much more flexible is the inventive coil than the other coils.

Three coils were measured. Coil A was a coil made according to the invention. Coils B and C are commercially available from Target Therapeutics Incorporated for a variety of uses. The coils' physical descriptions are as follows.

TABLE I

| COIL | COIL O.D. | WIRE Dia. | PITCH |
|---|---|---|---|
| A | 0.007" | 0.001" | 0.001" |
| B1 | 0.010" | 0.002" | 0.002" |
| B2 | 0.010" | 0.002" | 0.002+" |
| C | 0.015" | 0.003" | 0.003" |

"(physically stretched before measuring)

An introducer, a tapered length of tubing having an inside diameter of 0.010 inches, was taped to an angle template taken from an optical comparator. The respective coils were placed within the introducer and allowed to extend from the tip of the introducer at various lengths. The coils were extended to 1.0 cm and beyond. The introducer was held level and the angle between the tip of the introducer and the end of the coil was measured as a function of the length of the coil extending from the introducer. The results of the tests are shown in Table II below and in FIG. 6.

TABLE II

| COIL⇒ extension (mm) ⇓ | A (°) | B1 (°) | B2 (°) | C (°) |
|---|---|---|---|---|
| 1 | 0.75 | 0 | 0 | — |
| 2 | 4.0 | 2 | 0 | — |
| 3 | 5.5 | 2 | 0 | — |
| 4 | 10.0 | 2 | 0 | — |
| 5 | 18.5 | 2 | 1 | — |
| 6 | 24.5 | 2 | 2 | — |
| 7 | 33.5 | 2 | 3.5 | — |
| 8 | 42.5 | 3 | 4 | — |
| 9 | 45 | 3 | 7 | — |
| 10 | 51 | 3 | 13 | — |
| 20 | 69 | 20 | — | 26.5 |
| 30 | 80 | 51 | — | 47 |
| 40 | 84 | 65 | — | — |
| 50 | 88 | 73 | — | 72 |

The depicted data for the inventive Coil A and the Coil C are averages of a number of measurements of similar coils.

The relationship between the extension of the coils and their resulting deflection in degrees is shown in FIG. 6. It is readily observed that, at a 10 mm extension, the angle of deflection for the inventive coil is about 50°. For the other coils, the deflection is typically only about 10% of that value. Consequently, it may be understood that the bending radius of the inventive coil is much smaller, the force needed to bend the coil is significantly smaller, and consequently the coil will move through tortuous pathways both in the vasculature and in the catheter with significantly more ease than would be observed by the other coils.

Many alterations and modifications may be made by those of ordinary skill in the art without departing from the spirit and scope of the invention. The illustrated embodiments have been shown only for purposes of clarity and examples, and should not be taken as limiting the invention as defined by the following claims, which include all equivalents, whether now or later devised.

We claim as our invention:

1. A flexible, vaso-occlusive device for forming an occlusion in a selected site of the vasculature, said device having a size and flexibility such that the device may be safely delivered to a selected site in the vasculature of the human body by hydraulic delivery, where the device deflects more than about 35° under its own weight when one centimeter length of the device is supported horizontally at one end.

2. The device of claim 1 where the length of the device is between 2 mm and 120 cm.

3. The device of claim 1 having a preformed shape.

4. A flexible, vaso-occlusive device for forming an occlusion in a selected site of the vasculature, said device having a size and flexibility such that the device may be safely delivered to a selected site in the vasculature of the human body by hydraulic delivery, wherein the flexible vaso-occlusive device comprises a coil or a braid having an outside diameter less than about 0.010 inches, wherein the coil or braid is sufficiently flexible that a one centimeter length of the coil or braid supported horizontally at one end will deflect more than about 20° under its own weight.

5. The device of claim 4 comprising silver, gold, palladium, platinum, tungsten, iridium, stainless steel, or alloys thereof.

6. The device of claim 5 comprising an alloy of platinum and tungsten.

7. The device of claim 5 where device comprises ribbon, said ribbon having a major axis of 0.001 to 0.002 inches and a minor axis of 0.0005 to 0.001 inches.

8. The device of claim 4 where the device is regularly wound.

9. The device of claim 4 where the device is not regularly wound.

10. The device of claim 4 where the outside diameter is between about 0.0014 inches and about 0.0095 inches.

11. The device of claim 10 where the outside diameter is between about 0.004 inches and about 0.0095 inches.

12. The device of claim 11 where the outside diameter is between about 0.004 inches and about 0.0075 inches.

13. The device of claim 4 where the device comprises a filament, said filament having a filament with a diameter of less than 0.0025 inches.

14. The device of claim 13 where the device comprises a filament, said filament having a diameter of between 0.00045 and less than 0.00225 inches.

15. The device of claim 14 where the device comprises a filament, said filament having a diameter of between 0.0005 and 0.002 inches.

16. The device of claim 15 where the device comprises a filament, said filament having a diameter of between 0.001 and 0.002 inches.

17. The device of claim 14 where the length of the device is between 30 cm and 120 cm.

18. A flexible, vaso-occlusive device of a size and flexibility safely deliverable to a selected site in the vasculature of the human body by hydraulic delivery where the device deflects more than about 35° under its own weight when one centimeter length of the device is supported horizontally at one end.

* * * * *